United States Patent [19]
Avraham et al.

[11] Patent Number: 5,980,893
[45] Date of Patent: Nov. 9, 1999

[54] AGONIST MURINE MONOCLONAL ANTIBODY AS A STIMULANT FOR MEGAKARYOCYTOPOIESIS

[75] Inventors: Hava Avraham; Jerome E. Groopman, both of Brookline, Mass.

[73] Assignee: Beth Israel Deaconess Medical Center, Inc., Boston, Mass.

[21] Appl. No.: 08/895,626

[22] Filed: Jul. 17, 1997

[51] Int. Cl.$^6$ .............................. C07K 16/28; C12N 5/12
[52] U.S. Cl. .................................. 424/144.1; 424/133.1; 424/135.1; 424/142.1; 424/143.1; 424/153.1; 424/178.1; 424/93.7; 435/70.21; 435/334; 435/343; 530/387.3; 530/388.15; 530/388.2; 530/388.22; 530/388.7; 530/389.6; 530/391.1
[58] Field of Search .............................. 424/93.7, 133.1, 424/135.1, 142.1, 143.1, 144.1, 153.1, 178.1; 435/70.21, 334, 343; 530/387.3, 388.15, 388.2, 388.22, 388.7, 389.6, 391.1

[56] References Cited

U.S. PATENT DOCUMENTS

| | | | |
|---|---|---|---|
| 4,626,507 | 12/1986 | Trowbridge | 435/343 |
| 4,710,457 | 12/1987 | Dupont | 530/388.75 |
| 5,635,388 | 6/1997 | Bennett | 435/334 |

FOREIGN PATENT DOCUMENTS

| | | |
|---|---|---|
| WO9518858 | 7/1995 | WIPO . |

OTHER PUBLICATIONS

Drexler HG and Quentmeier H, Thrombopoietin: expression of its receptor MPL and proliferative effects on leukemic cells. Leukemia 10:1405–1421, 1996.

Parren PWHI, Preparation of genetically engineered monoclonal antibodies for human immunotheraphy. Hum Antibod Hybridomas 3:137–145, 1992.

Debili N, The MPL receptor is expressed in the megakaryocytic lineage from late progenitors to platelets, 85:2, 391–401, Jan. 15, 1995.

Borrebaeck CAK, Strategey for the production of human monoclonal antibodies using in vitro activated B cells. J. Immunol Meth. 123:157–165, 1989.

Avraham et al., "Modulation of megakaryocytopoiesis by human basic fibroblast growth factor," *Blood*, vol. 83, No. 8:pp. 2126–2132 (1994).

Avraham et al., "Interacation of human bone marrow fibroblasts with megakaryocytes: role of the c–kit ligand," *Blood* vol. 80, No.7:pp. 1679–1684 (1992).

Azrin et al., "Preparation, characterization, and evaluation of a monoclonal antibody against the rabbit platelet glycoprotein IIb/IIIa in an experimental angioplasty model," *Circulation Research* vol. 75:pp. 268–277 (1994).

Banu et al., "Modulation of megakaryocytopoiesis by thrombopoietin: the c–Mpl ligand," *Blood* vol. 86, No.4:pp. 1331–1338 (1995).

Barclay et al., "Rapid isolation of monoclonal antibodies specific for cell surface differentiation antigens," *Proc. Natl. Acad. Sci. USA* vol. 83:pp. 4336–4340 (1986).

Bartley et al., "Identification and cloning of a megakaryocyte growth and development factor that is a ligand for the cytokine receptor Mpl," *Cell* vol. 77:pp. 1117–1124 (1994).

Broudy et al., "Thrombopoietin (c–mpl ligand) acts synergistically with erythropoietin, stem cell factor, and interleukin–11 to enhance murine megakaryocyte colony growth and increases megakaryocyte ploidy in vitro," *Blood* vol. 85, No.7:pp. 1719–1726 (1995).

Choi et al., "Platelets generated in vitro from proplatelet–displaying human megakaryocytes are functional," *Blood* vol. 85:pp. 402–413 (1995).

Coller, "Diagnostic and therapeutic applications of anti–platelet monoclonal antibodies," *Biorheology* vol. 24:pp. 649–658 (1987).

Coller et al., "A murine monoclonal antibody that completely blocks the binding of fibrinogen to platelets produces a thrombasthenic–like state in normal platelets and binds to glycoproteins IIb and/or IIIa," *J. Clin.Invest.* vol. 72:pp. 325–338 (1983).

Debili et al., "The Mpl–ligand or thrombopoietin or megakaryocyte growth and differentiative factor has both direct proliferative and differentiative activities on human megakaryocyte progenitors," *Blood* vol. 86, No.7:pp. 2516–2525 (1995).

Derg et al., *Exp. Hematol.* vol. 24:pp. 1072, Abstr. 260, Aug. 23–27, 1996.

de Sauvage et al., "Stimulation of megakaryocytopoiesis and thrombopoiesis by the c–Mpl ligand," *Nature* vol. 369:pp. 533–538 (1994).

de Sauvage et al., "Physiological regulation of early and late stages of megakaryocytopoiesis by Thrombopoietin," *J. Exp. Med.* vol. 183:pp. 651–656 (1996).

Gilbert et al., "Production of a human monoclonal anti–epithelial cell surface antibody derived from a patient with Pemphigus Vulgaris," *Journal of Autoimmunity* vol. 5:pp. 173–182 (1992).

(List continued on next page.)

*Primary Examiner*—David Saunders
*Assistant Examiner*—Mary Beth Tung
*Attorney, Agent, or Firm*—Weingarten, Schurgin, Gagnebin & Hayes LLP

[57] ABSTRACT

A class of murine monoclonal antibodies that is capable of stimulating megakaryocytopoiesis in vitro has been raised against human megakaryocytic cells. The monoclonal antibody BAH-1 specifically recognizes and demonstrates agonist activity against the c-Mpl receptor on the megakaryocytic cell surface. In therapeutic applications, the BAH-1 and M4 monoclonal antibodies identified to date and similar antibodies (or active portions and chimeric combinations thereof) can stimulate proliferation of primary bone marrow megakaryocytes. Thus, the antibodies of the invention can be used to prepare a composition for treating, e.g., thrombocytopenia. A typical composition comprises a therapeutically effective amount of the BAH-1 monoclonal antibody in association with a pharmaceutically acceptable carrier vehicle.

12 Claims, 5 Drawing Sheets

OTHER PUBLICATIONS

Grossman et al., "Thrombopoietin accelerates platelet, red blood cell, and neutrophil recovery in myelosuppressed mice," *Experimental Hematology* vol. 24:pp. 1238–1246 (1996).

Gurney et al., "Thrombocytopenia in c–mpl–deficient mice," *Science* vol. 265:pp. 1445–1447 (1994).

Kaushansky et al., "Thrombopoietin expands erythroid progenitors, increases red cell production, and enhances erythroid recovery after myelosuppressive therapy," *J. Clin. Invest.* vol. 95:pp. 1683–1687 (1995).

Kaushansky et al., "Thrombopoietin, the Mpl ligand, is essential for full megakaryocyte development," *Proc. Natl. Acad. Sci. USA* vol. 92:pp. 3234–3238 (1995).

Kaushansky et al., "Thrombopoietin expands erythroid, granulocyte–macrophage, and megakaryocytic progenitor cells in normal and myelosuppressed mice," *Experimental Hematology* vol. 24:pp. 265–269 (1996).

Kaushansky et al., "Promotion of megakaryocyte progenitor expansion and differentiation by the c–Mpl ligand thrombopoietin," *Nature* vol. 369:pp. 568–571 (1994).

Komatsu et al., "Growth and differentiation of a human megakarylblastic cell line, CMK," *Blood* vol. 74:pp. 42–48 (1989).

Kuter et al., "The purification of megapoietin: a physiological regulator of megakaryocyte growth and platelet production," *Proc. Natl. Acad. Sci. USA* vol. 91:pp. 11104–11108 (1994).

Lok et al., "Cloning and expression of murine thrombopoietin cDNA and stimulation of platelet production in vivo," *Nature* vol. 369:pp. 565–568 (1994).

Methia et al., "Oligodeoxynucleotides Antisense to the Proto–oncogene c–mpl Specifically Inhibit In Vitro Megakaryocytopoiesis," *Blood* vol. 82, No. 5: pp. 1395–1401 (1993).

Meyer et al., "Isolation and characterization of monoclonal antibodies directed against plant plasma membrane and cell wall epitopes: identification of a monoclonal antibody that recognizes extensin and analysis of the process of epitope biosynthesis in plant tissues and cell cultures," *Journal of Cell Biology* vol. 107:pp. 163–175 (1988).

Mignotte et al., "Structure and Transcription of the Human c–mpl Gene (MPL)," *Genomics* vol 20:pp. 5–12 (1994).

Reverter et al., "Inhibition of Platelet–mediated, Tissue Factor–induced Thrombin Generation by the Mouse/Human Chimeric 7E3 Antibody," *J. Clin. Invest.* vol. 98, No. 3:pp. 863–874 (1996).

Scudder et al., "Preparation and Functional Characterization of Monoclonal Antibodies against Clycoprotein Ib," *Blood* 61:99 (1983).

Vigon et al., "Characteriztion of the murine Mpl proto–oncogene, a member of the hematopoietic cytokine receptor family: molecular cloning, chromosomal location and evidence for a function in cell growth," *Oncogene* vol 8:pp. 2607–2615 (1993).

Vigon et al., "Molecular cloning and characterization of MPL, the human homology of the v–mpl oncogene: Identification of a member of the hematopoietic growth factor receptor superfamily," *Proc. Nant. Acad. Sci.* vol. 89: pp. 5640–5644 (1992).

Wendling et al., "cMpl ligand is a humoral regulator of megakaryocytopoiesis," *Nature* vol. 369:571–574 (1994).

Zeigler et al., "In vitro megakaryocytopoietic and thrombopoietic activity of c–mpl ligand (TPO) on purified murine hematopoietic stem cells," *Blood* vol. 84:pp. 4045–4052 (1994).

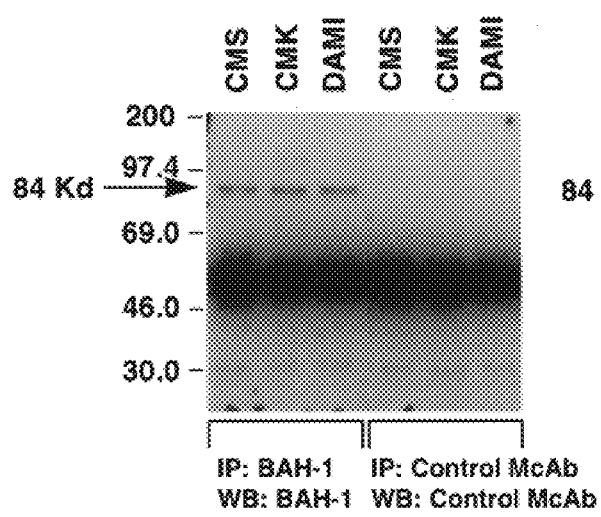 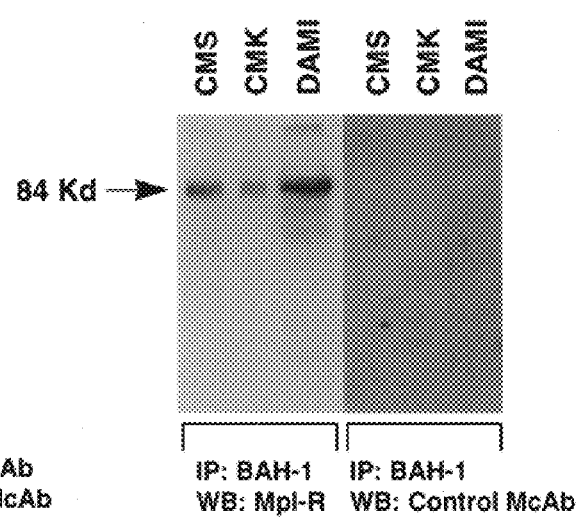
*FIG. 1A*  *FIG. 1B*

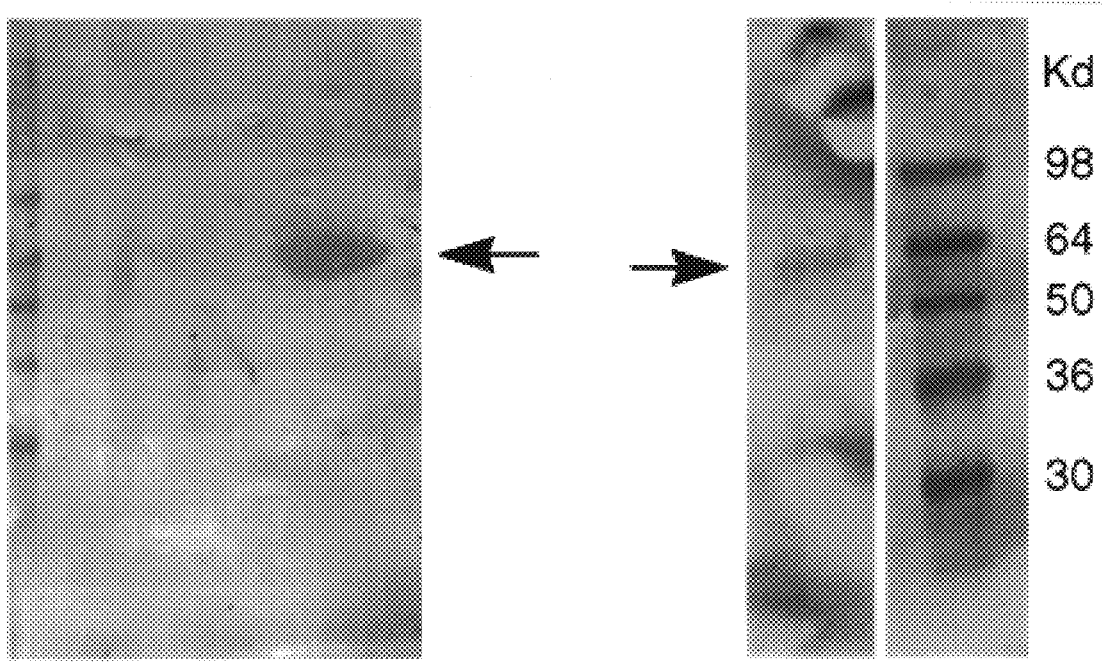
*FIG. 2A*  *FIG. 2B*

AGONIST MURINE MONOCLONAL ANTIBODY AS A STIMULANT FOR MEGAKARYOCYTOPOIESIS

FIELD OF THE INVENTION

This invention relates to the treatment of thrombocytopenia, and more particularly to the use of an agonist antibody capable of stimulating megakaryocytopoiesis for such treatment.

BACKGROUND OF THE INVENTION

The development of specialized blood cells, including platelets, via the hematopoietic system requires the interplay of pluripotent cells found in bone marrow and polypeptide cytokines (5). When a patient's levels of circulating platlets are depleted to less than $150 \times 10^9$ platlets per liter, a condition known as thrombocytopenia can follow. In general, patients with platelet counts between 20 and $100 \times 10^9$ per liter are at risk of excessive post traumatic bleeding, while those with platelet counts below $20 \times 10^9$ may bleed spontaneously. These latter patients are candidates for platelet transfusion with associated immune and viral risk.

The major regulator of circulating levels of platelets in the blood is believed to be the recently cloned cytokine thrombopoietin (TPO), the cognate ligand for the receptor encoded by the c-mpl proto-oncogene (c-Mpl) (1–16). TPO has been determined to have both direct proliferative and differentiative activities on human megakaryocyte progenitors. Furthermore, TPO hastens the restoration of platelet counts following cytoreductive therapies and has been associated with improved survival in certain murine models. Treatment of patients suffering from thrombocytopenia with TPO should have therapeutic importance in augmenting megakaryocytopoiesis and circulating blood platelet numbers. The availability of additional agents, capable of stimulating platelet production would be desirable.

SUMMARY OF THE INVENTION

Using a novel procedure for eliciting murine monoclonal antibodies to various cells of hemopoietic lineage, we have generated agonist murine monoclonal antibodies against surface antigens of human megakaryocytic cells. This new class of monoclonal antibodies, represented specifically by the monoclonal antibodies BAH-1 and M4 which are more particularly described below, is capable of stimulating proliferation of primary bone marrow megakaryocytes.

The specific monoclonal antibody BAH-1, furthermore, shows agonist activity in various assays of in vitro human and murine megakaryocytopoiesis; in the generation of megakaryocyte progenitors, CFU-MK; and in the production of mature GpIIb/IIIa expressing megakaryocytes in liquid cultures of heterogeneous bone marrow cells. From these and other results reported below, we can conclude that the newly isolated murine monoclonal antibody BAH-1 specifically recognizes and activates the human c-Mpl receptor, thereby transducing signals to regulate megakaryocyte growth and maturation.

Thus, in one aspect, the invention is directed to an agonist monoclonal antibody that specifically recognizes human megakaryocytes and is capable of stimulating megakaryocytopoiesis in vitro. Preferably, the agonist monoclonal antibody of the invention is a monoclonal antibody raised against live human megakaryocytic cells that specifically recognizes and demonstrates agonist activity against the c-Mpl receptor on megakaryocytic cells. Most preferably, the agonist monoclonal antibody of the invention is the monoclonal antibody BAH-1 produced by the hybridoma cell line ATCC No. HB 12027; or a monoclonal antibody that binds to the same antigenic determinant as a monoclonal antibody produced by the hybridoma cell line ATCC No. HB 12027; or an Fab, F(ab')$_2$, or Fv fragment or conjugate of a monoclonal antibody produced by the hybridoma cell line ATCC No. HB 12027.

In another aspect, the monoclonal antibody of the invention is preferably the monoclonal antibody M4 produced by the hybridoma cell line ATCC No. HB 12353; or a monoclonal antibody that binds to the same antigenic determinant as a monoclonal antibody produced by the hybridoma cell line ATCC No. HB 12353; or an Fab, F(ab')$_2$, or Fv fragment or conjugate of a monoclonal antibody produced by the hybridoma cell line ATCC No. HB 12353.

In a further aspect, the invention features a method of generating an agonist monoclonal antibody that specifically recognizes any chosen cell of hemopoietic lineage. The method includes an immunization step using primary cells of a chosen cell type. Preferably, the method also includes one or more immunization steps using live cells of an immortalized cell line of a chosen cell type and a final immunization step using primary cells of the chosen cell type. Preferably, the chosen cell type is megakaryocytic cells, for which the immortalized cells are of a human megakaryocytic cell line, e.g. CMK, Mo7e, CMS or DAMI, with the primary cells being human megakaryocytic cells. Alternatively, the chosen cell type is stem cells, B cells or T cells for which the immortalized cell lines can be, e.g., the stem cell line CTS, the B cell lines ARH-77 or SB or Nal-6, or the T cell lines Jurkat or H9. Such agonist antibodies can be used to stimulate growth factor receptors and enhance colony formation of either monocytes, macrophages, B cells, T cells, megakaroyocytes and platelets in various leukemia and various hematopoietic deficiencies.

In therapeutic applications, the BAH-1 monoclonal antibody or M4 monoclonal antibody identified to date and similar antibodies (or active portions and chimeric combinations thereof) can stimulate proliferation of primary bone marrow megakaryocytes. Thus, the antibodies of the invention preferably can be used to prepare a composition for treating, e.g., thrombocytopenia. Such a composition comprises a therapeutically effective amount of the agonist monoclonal antibody of the invention in association with a pharmaceutically acceptable carrier vehicle. Preferably, the agonist monoclonal antibody included in the therapeutic composition is the monoclonal antibody BAH-1.

Recombinant human thrombopoietin is currently being tested in clinical trials for its therapeutic effectiveness in augmenting megakaryocytopoiesis and circulating blood platelet numbers in patients suffering from thrombocytopenia. The agonist murine monoclonal antibodies of the invention that are capable of stimulating proliferation of primary bone marrow megakaryocytes will serve as an attractive addition to the therapeutic arsenal for situations where a prolonged half-life of the administered agent, and thus less frequent administration, is desired. Because of the prolonged half-life of antibodies, it would be feasible to administer an agonist monoclonal antibody, e.g., an antibody to the c-Mpl receptor, to a patient on an intermittent basis, thereby sustaining stimulation of megakaryocytopoiesis in patients with compromised production of cells in this lineage. This approach can be readily modeled in preclinical animal studies of compromised bone marrow function in the setting of chemotherapy, radiation therapy, and antiplatelet antibodies.

Other features and advantages of the invention will be apparent from the following description of the preferred embodiments thereof and from the claims.

BRIEF DESCRIPTION OF THE DRAWINGS

FIGS. 1A and 1B show immunoprecipitation of Mpl receptor protein;

FIG. 2A and 2B show mapping of the site of binding of the BAH-1 monoclonal antibody of the invention to the C-Mpl receptor;

DETAILED DESCRIPTION OF THE INVENTION

Figure 3:
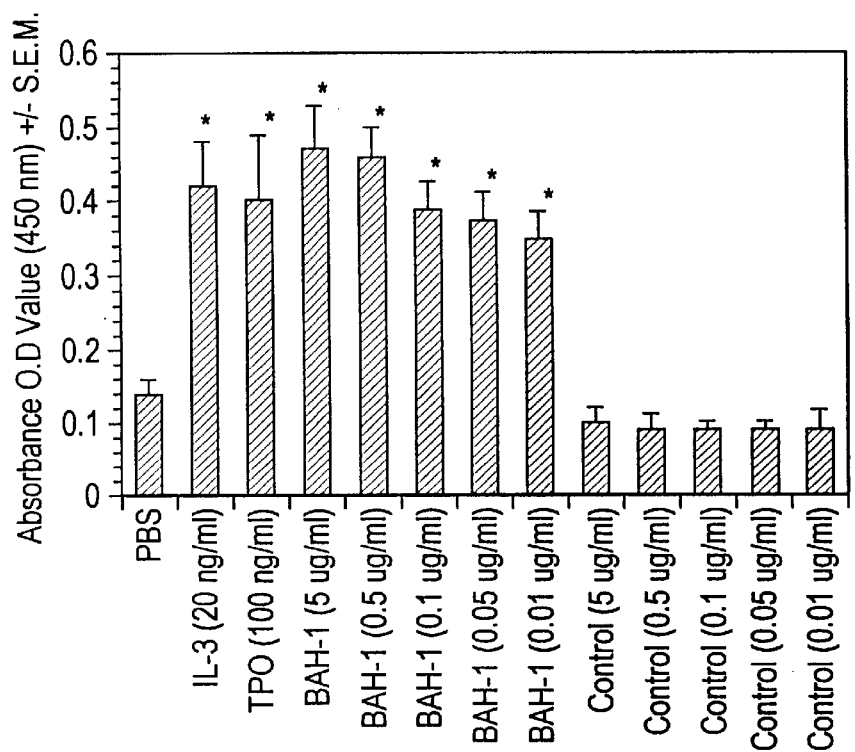
FIG. 3 shows the effect of TPO, IL-3 and BAH-1 monoclonal antibody on megakaryocytopoiesis in a dynamic heterogeneous liquid culture system.

The monoclonal antibodies of the invention can be prepared by hybridoma fusion techniques or by techniques that utilize Epstein Barr Virus (EBV) -immortalization technologies (to produce human mAbs), such as are well known by those of skill in the art, modified as described herein. In the method of the invention, these techniques involve the injection of a live cell immunogen, in other words, live cells of an immortalized cell line of the chosen cell type of hemopoietic lineage, into an animal (e.g., a mouse) so as to elicit a desired immune response in that animal (i.e., production of antibodies). The experimental animal, (e.g., a mouse) is given repeated injections (boosts) of the same immortalized cell line. In a final step, the animal is given an injection of primary cells of the chosen cell type. The final injection could also include cells of the previously used immortal cell line. If primary cells of the chosen cell type are available in quantity, all immunization injections could be of such cells.

In the illustrative example herein for the production of agonist monoclonal antibodies to megakaryocytic cells, a CMK cell preparation and a CMS cell preparation were used as the first immunogens; however, other immortalized megakaryocytic cells, such as Mo7e or DAMI cells, could have been used. Other monoclonal antibodies analogous to the agonist antibody of the invention BAH-1, which specifically recognizes the C-Mpl receptor, can be generated using membrane bound c-Mpl receptor protein as the immunogen. To generate agonist monoclonal antibodies against other cell types, other cells of hemopoietic lineage are chosen, e.g., stem cells, B cells or T cells. In the first immunization step stem cells can be represented, e.g., by the immortalized cell line CTS; B cells by the immortalized cell lines ARH-77, SB or Nal-6; and T cells by the immortalized cell lines Jurkat or H9.

After a sufficient time, the animal is sacrificed and somatic antibody-producing cells may be derived from the lymph nodes, spleens and peripheral blood of primed animals. Spleen cells are preferred. Mouse lymphocytes give a higher percentage of stable fusions with the mouse myelomas described below. The use of rat, rabbit, frog, sheep and other mammalian somatic cells is also possible. The spleen cell chromosomes encoding desired immunoglobulins are immortalized by fusing the spleen cells with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653 or Sp2/O-Ag14 myeloma lines. These myeloma lines are available from the American Type Culture Collection (ATCC), 10801 University Boulevard, Manassas, Va. 20110-2209.

The resulting cells, which include the desired hybridomas, are then grown in a selective medium, such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques such as those described herein, using the antigen that has been used for immunization. Positive clones can then be subcloned under limiting dilution conditions and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography. Hybridomas produced according to these methods can be propagated in vitro or in vivo (in ascites fluid) using techniques known in the art (see, generally, Harlow et al., Antibodies. A Laboratory Manual, Cold Spring Harbor Laboratory, pp. 1–726, 1988).

Generally, the individual cell line may be propagated in vitro, for example in laboratory culture vessels, and the culture medium containing high concentrations of a single specific monoclonal antibody can be harvested by decantation, filtration or centrifugation. Alternatively, the yield of monoclonal antibody can be enhanced by injecting a sample of the hybridoma into a histocompatible animal of the type used to provide the somatic and myeloma cells for the original fusion. Tumors secreting the specific monoclonal antibody produced by the fused cell hybrid develop in the injected animal. The body fluids of the animal, such as ascites fluid or serum, provide monoclonal antibodies in high concentrations. As discussed by Cole et al., supra, when human hybridomas or EBV-hybridomas are used, it is necessary to avoid rejection of the xenograft injected into animals such as mice. Immunodeficient or nude mice may be used or the hybridoma may be passaged first into irradiated nude mice as a solid subcutaneous tumor, cultured in vitro and then injected intraperitoneally into pristine primed, irradiated nude mice which develop ascites tumors secreting large amounts of specific human monoclonal antibodies (see Cole et al., supra).

For certain therapeutic applications chimeric (mouse-human) or human monoclonal antibodies may be preferable to murine antibodies, because patients treated with mouse antibodies generate human antimouse antibodies, (Shawler et al., *J. Immunol.* 135: 1530–35 (1985)). Chimeric mouse-human monoclonal antibodies showing agonist activity, e.g., to the c-Mpl receptor can be produced, for example, by the techniques of Oi et al., *Biotechnologies* 4(3): 214–221 (1986) or Liu et al., *Proc. Nat'l. Acad. Sci.* (*USA*) 84: 3439–43 (1987). Accordingly, genes coding for the constant regions of molecules of a murine antibody of the invention are substituted with human genes coding for the constant regions of an antibody with appropriate biological activity (such as the ability to activate human complement and mediate antibody dependent cellular cytotoxicity (ADCC)).

It should be understood that the present invention, furthermore, encompasses the deposited BAH-1 and M4 monoclonal antibodies described above and any fragments thereof containing the active binding region of the antibody, such as Fab, F(ab')$_2$ and Fv fragments. Such fragments can be produced from the antibody using techniques well established in the art (see, e.g., Rousseaux et al., in *Methods Enzymol.* 121: 663–69 Academic Press, (1986)).

In addition, the present invention encompasses antibodies that are capable of binding to the same antigenic determinants as the deposited antibodies already identified and competing with the deposited antibodies for binding at those sites. These include antibodies having the same antigenic specificity as the BAH-1 or M4 antibodies of the invention, but differing in species origin or isotype. For example, class, isotype and other variants of the antibody of the invention may be constructed using recombinant class-switching and fusion techniques known in the art (see, e.g., Thammana et al., *Eur. J. Immunol.* 13: 614 (1983); Spira et al., *J. Immunol. Meth.* 74: 307–15 (1984); Neuberger et al., Nature 312: 604–08 (1984); and Oi et al., supra)). Thus, chimeric antibodies or other recombinant antibodies (e.g., antibody fused to a second protein such as a lymphokine) having the same agonist specificity as the BAH-1 antibody or the M4 antibody fall within the scope of this invention.

Chimeric or other recombinant antibodies or fragments thereof of the invention, as described above, may be used therapeutically. For example, a fusion protein comprising at least the antigen-binding region of a BAH-1 or M4 antibody may be joined to a portion of a second carrier protein. In addition, a chimeric BAH-1 or M4 antibody may be formed wherein the antigen-binding region may be joined to portions or fragments of a human Ig molecule. Furthermore, recombinant techniques known in the art can be used to construct bispecific antibodies wherein one of the binding specificities of the antibody is that of BAH-1 or M4 (see, e.g., U.S. Pat. No. 4,474,893).

It is apparent therefore that the present invention encompasses pharmaceutical compositions, combinations and methods for stimulating proliferation of primary bone marrow megakaryocytes. For example, the invention includes pharmaceutical compositions for use in the treatment of thrombocytopenia comprising a pharmaceutically effective amount of, e.g, a BAH-1 or M4 antibody in a pharmaceutically acceptable carrier. The compositions may contain the chosen antibody, either unmodified, conjugated to a second protein or protein portion, or in a recombinant form (e.g., chimeric or bispecific BAH-1). The compositions may additionally include other antibodies or conjugates, or other therapeutic agents.

The following examples are presented to illustrate the advantages of the present invention and to assist one of ordinary skill in making and using the same. These examples are not intended in any way otherwise to limit the scope of the disclosure.

EXAMPLE I

Isolation and Characterization of the Monoclonal Antibodies BAH-1 and M4

After screening approximately 6000 hybridomas, we have derived a protocol for producing monoclonal antibodies of the invention. BALB/c mice (from Jackson Laboratories, Bar Harbor, Me.) were given repeated injections of $1\times10^7$ CMK or CMS cells emulsified in complete Freunds adjuvant according to a previously reported protocol (17–21) in two separate immunization experiments. A final booster of $2\times10^5$ human primary bone marrow megakaryocytes plus $1\times10^6$ cells of the previously used immortal cell line was injected 3–4 days before the animals were sacrificed.

Approximately $1\times10^8$ spleen cells from the immunized mice were fused with $2\times10^7$ myeloma cells from a mouse myeloma cell line (X653) by the addition of 1 ml of 40% polyethylene glycol (1500, Baker). The fused cells were then diluted with 15 ml of Dulbecco's modified Eagle's medium (DMEM), centrifuged, and rediluted into complete (10% fetal calf serum) selective medium containing hypoxanthine/aminopterin/thymidine at $2\times10^6$ cells/ml. The cells were then distributed into 96 wells (100 µl) in hypoxanthine/aminopterin/thymidine medium (18).

After 10–16 days, when sufficient cell growth had occurred to begin acidification of the medium, duplicate aliquots of the supernatants were assayed for cell ELISA binding. Hybridoma cells from positive testing wells were then transferred to 24 wells containing 0.5 ml of hypoxanthine and thymidine medium. After the cells were grown and retested, they were cloned and recloned by limiting dilution into 96-well plates. For antibody assays, the supernatants from the hybridoma cells were tested directly.

A screening procedure using a whole cell ELISA technique (22–23) was employed to detect antibodies which specifically recognized the human megakaryocytic cell lines CMK, DAMI, Mo7e and CMS but did not recognize T cells, B cells and monocyte-macrophages. Following identification of three candidate anti-megakaryocyte antibodies out of 400 hybridomas tested, we conducted cross-blocking screening studies to eliminate antibodies recognizing known megakaryocytic surface structures by using a panel of antibodies against the integrins GpIb and GpIIb/IIIa (22–23). Murine monoclonal antibodies BAH-1 and M4, which appeared to be specific for megakaryocytes and did not recognize such known integrin surface structures, were further characterized.

Monoclonal antibodies which appeared specific for human megakaryocytes were isotyped using a panel of specific anti-murine immunoglobulin antisera (Innoliamouse McAb isotyping kit, Innogenetics). Both the murine monoclonal antibodies BAH-1 and M4 were found to be IgG1 kappa.

To determine additional properties of the monoclonal antibodies of the invention, BAH-1 hybridoma cells were injected intraperitoneally into BALB/c mice primed with pristine, and the antibody-containing ascites fluid was collected 2–3 weeks later. The antibody was affinity purified as described (22). Immunofluorescence staining for antigen expression was evaluated using BAH-1 monoclonal antibodies and Mpl-R monoclonal antibodies (commercially available from Genzyme, Inc., Cambridge, Mass.), CD61 or control monoclonal antibody in a Dami human megakaryocytic cell line as well as in Jurkat T cells. More than 90% of the CMK, Mo7e, CMS and DAMI megakaryocytic cells were positive. No staining was observed when Jurkat T cells or Ramos B cells were stained.

Immunoprecipitation and Western blot analysis revealed that BAH-1 reacted specifically with the recombinant c-Mpl protein. Referring to FIGS. 1A and 1B, CMK cells were lysed and the cell extracts immunoprecipitated with BAH-1 antibodies. Lanes 4–6 represent precipitation with control monoclonal antibody. The SDS-PAGE transfer was then subjected to immunoblotting with Mpl-R or BAH-1 antibodies as described in Materials and Methods (below). Arrow indicates the position of the Mpl-R protein. The reactive proteins were detected using ECL system (Amersham). CMK cell lysates were incubated with BAH-1 and Mpl-R monoclonal antibodies. Immunoprecipitates were analyzed on 7.5% SDS-PAGE and immunoblotted with either BAH-1 or Mpl-R monoclonal antibodies. An 84 Kd protein was detected by both monoclonal antibodies revealed by these analyses, indicating that both monoclonal antibodies recognized the same protein, the Mpl-receptor.

Binding of BAH-1 monoclonal antibody to human Mpl-IgG and murine Mpl-IgG was determined by Western blot analysis. This antibody recognized both human and murine Mpl-IgG, confirming that BAH-1 recognizes the Mpl receptor of both species. In addition, referring to FIGS. 2A and 2B, in Western Blot analysis of domain 1 Mpl-IgG (FIG. 2A) and gD-Mpl (FIG. 2B), BAH-1 binding to c-Mpl was mapped to domain 1 of this receptor.

EXAMPLE II

Functional Characterization of the Monoclonal Antibody BAH-1

The effects of BAH-1 monoclonal antibody on hematopoiesis were elucidated. No effects were observed on CFU-GM colonies, BFU-E or CFU-E colonies when purified ascites of BAH-1 monoclonal antibody in various concentrations (1 ng/ml to 1 µg/ml) or supernatant of the BAH-1 hybridoma in various dilutions (1 ng/ml to 1 µg/ml) were tested. BAH-1 treatment over a range of concentrations (1, 10, or 50 ng/ml) increased CMK ploidy.

To evaluate the effect of BAH-1 monoclonal antibody, compared to TPO and IL-3, on CD34$^+$ cells, immunomagnetic bead-separated CD34$^+$ cells were cultured at a concentration of $5 \times 10^4$/ml in serum free medium. Referring to FIG. 3, non-adherent BM cells ($5 \times 10^4$/200 µL/well) were seeded in RPMI 1640 with 10% PPP in the presence of rhTPO or IL-3 950 µl/mg) or BAH-1 mcAb in various concentrations for 10 days at 37° C. in 5% $CO_2$. After 10 days, megakaryocytes were detected by cell ELISA using gpIIb/IIIa antibodies. Experiments were performed in triplicate in two experiments. The data are presented as the mean OD±SEM. After 10 days of culture in the presence of BAH-1, the number of megakaryocytes had increased to similar levels as those in the TPO cultures. A plateau was reached at 100 ng/ml of BAH-1 as compared to 100 ng/ml TPO. Therefore, BAH-1 alone can effect megakaryocytopoiesis in a dynamic heterogeneous liquid culture system.

Figure 4:
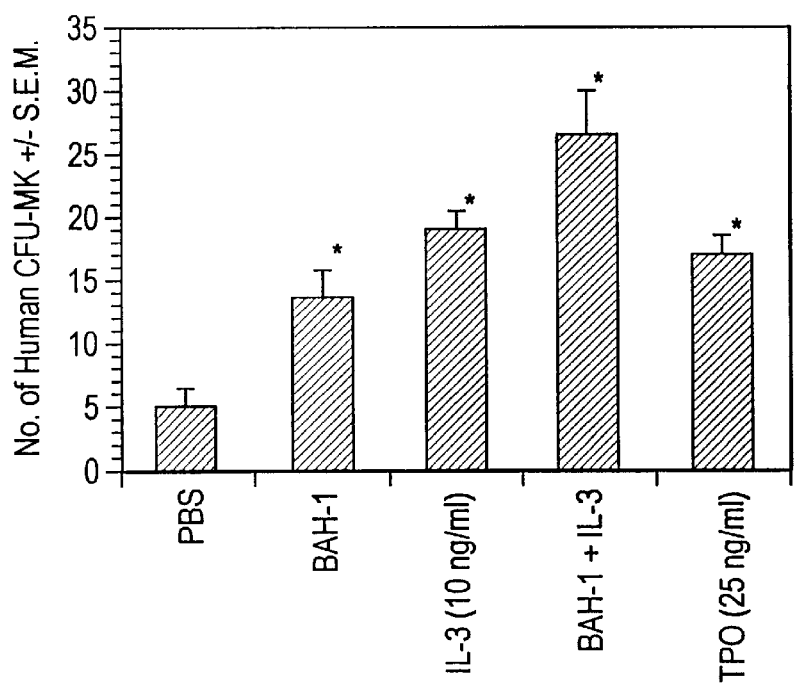
FIG. 4 shows the effect of BAH-1 monoclonal antibody on the proliferation of primary human megakaryocytes.

To examine further the biological effects of BAH-1 on primary progenitor cell growth, we evaluated clonogenic cultures of human CD34$^+$ progenitors in the fibrin clot system. CFU-MK derived colonies (CD34$^+$DR$^+$) appeared in the presence of hIL-3 and hTPO. BAH-1 alone also supported the formation of such megakaryocyte colonies. The combination of IL-3 plus BAH-1 significantly increased the number of human CFU-MK colonies, as shown in FIG. 4. Bone marrow CD34$^+$ cells were plated at $5 \times 10^3$/ml (see Materials and Methods), and the results are expressed as the means±SEM of megakaryocyte colonies.

We next studied the role of BAH-1 alone and in combination with IL-3 or hTPO in regulating the growth and maturation of a heterogeneous population of human bone marrow cells in this plasma clot assay. Nonadherent bone marrow cells were incubated in the presence of different concentrations of BAH-1 alone or with other cytokines. The numbers of CFU-MK colonies generated per culture were identified. BAH-1, hTPO or IL-3 alone resulted in the generation of identifiable megakaryocytes. These results further demonstrate that BAH-1 can effect megakaryocytopoiesis.

Figure 5:
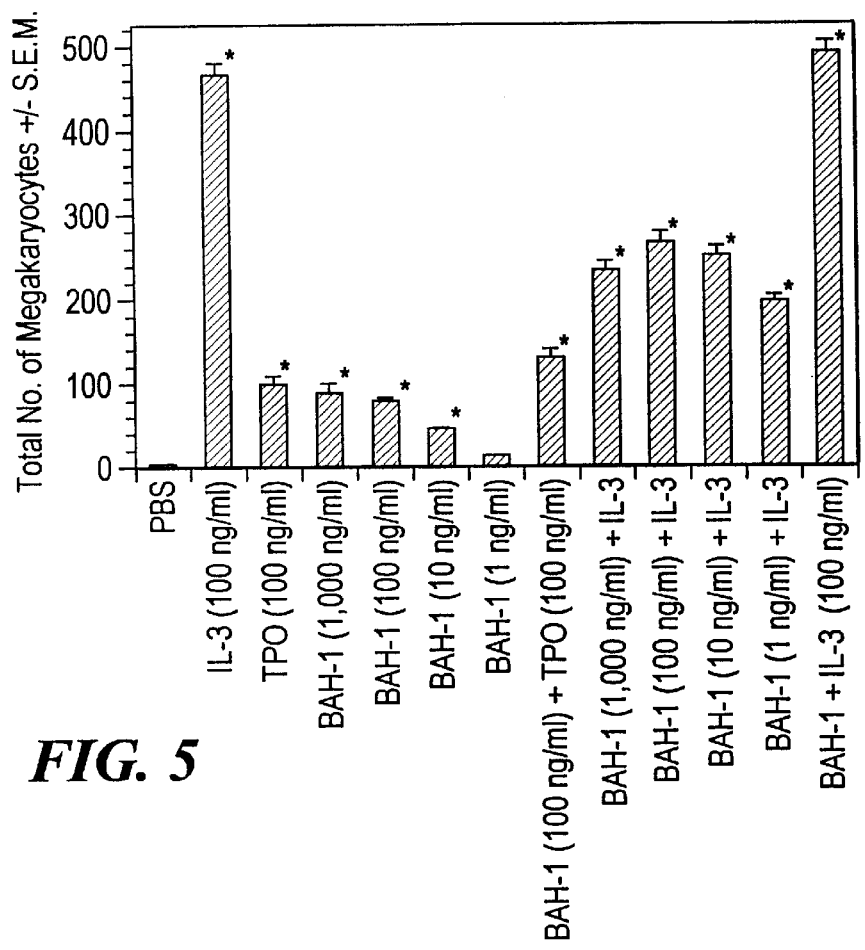
FIG. 5 shows a day 5 culture obtained from CD34$^+$CD41$^+$ cells with TPO or BAH-1 monoclonal antibody and observed under an inverted microscope.

In a limiting dilution experiment, CD34$^+$CD41$^+$ cells, grown in serum-free conditions, were plated at a concentration of 1–50 cells (100 µl volume) in the presence of TPO, IL-3 or various concentrations of BAH-1 alone, BAH-1 plus TPO, or BAH-1 plus IL-3. The average number of cells per well of a Day 5 culture was determined by observation of the cultures under an inverted microscope. As shown in FIG. 5, the effect of BAH-1 was similar to that of TPO. The percentage of positive megakaryocytes in each well was determined to be approximately 40–70%. Individual large megakaryocytes as well as small megakaryocytic cells were observed.

Figure 6:
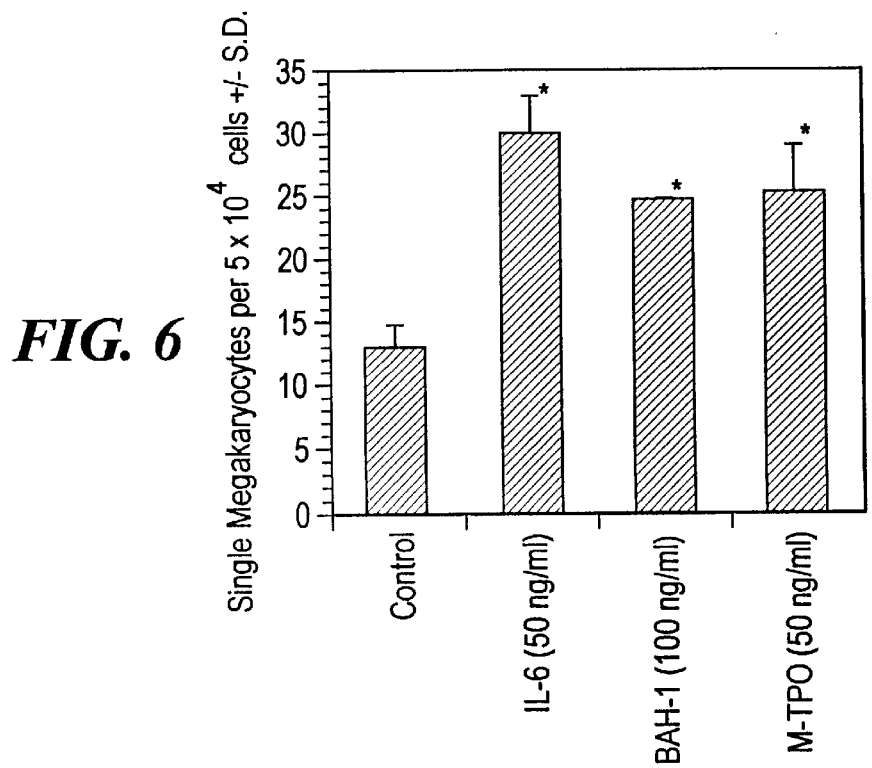
FIG. 6 shows the effect of BAH-1 monoclonal antibody on murine immature megakaryocytes using the single megakaryocyte growth assay.

The responsiveness of immature murine megakaryocytes to titrated doses of BAH-1 is shown in FIG. 6. Immature megakaryocytes showed a significant growth response to BAH-1 with an increase in detectable numbers of acetylcholinesterase-positive megakaryocytes using the single cell growth assay.

Figure 7:
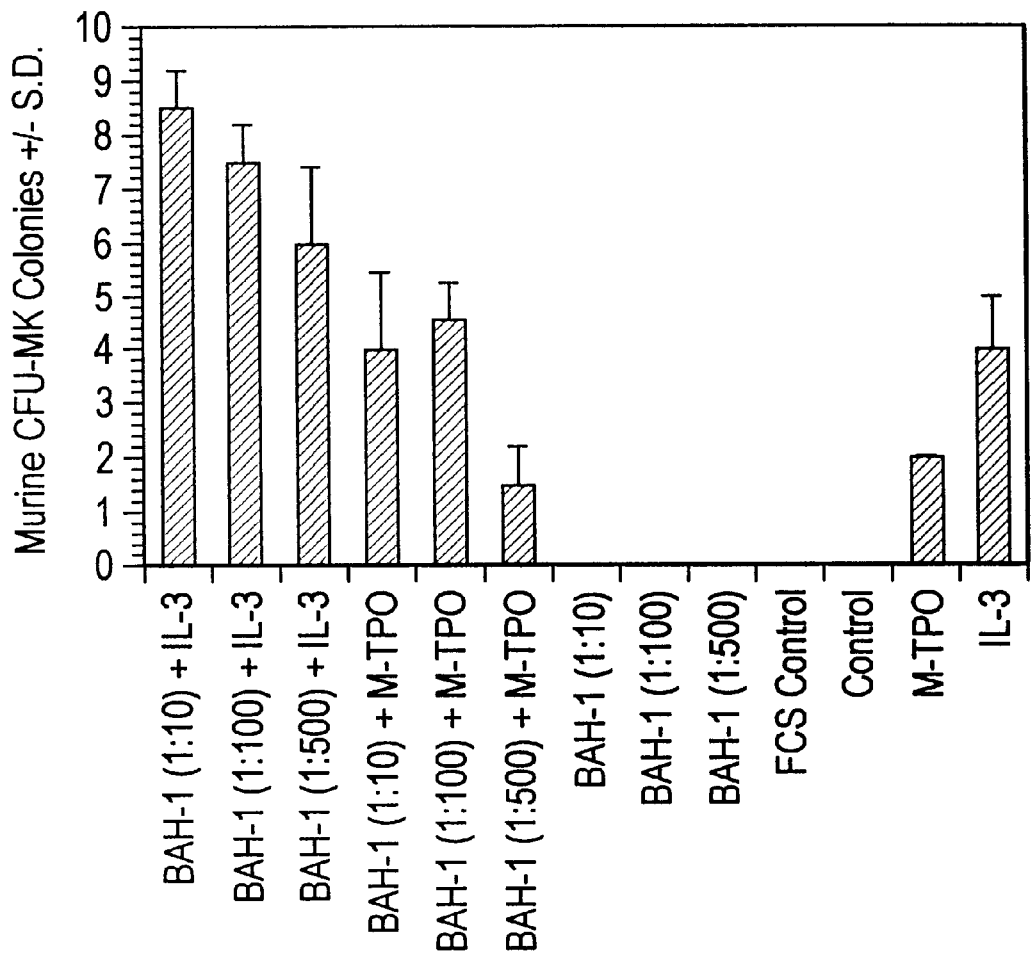
FIG. 7 shows the effect of BAH-1 monoclonal antibody on murine CFU-MK colonies.

The effect of BAH-1 on murine CFU-MK was also characterized. CFU-MK megakaryocytes were scored as the number of colonies with 3 cells or more per $10^5$ unfractionated cells. As shown in FIG. 7, BAH-1 alone failed to stimulate murine CFU-MK colony production. However, the addition of BAH-1 to cultures containing IL-3 or TPO significantly (P<0.05) increased the CFU-MK formation.

The effects of BAH-1 alone or in combination with TPO on hematopoietic progenitor cell numbers during the recovery phase following myelosuppressive therapy were evaluated in myelosuppressed mice. As shown in Table 1, an increase in the numbers of CFU-MK colonies was observed in the bone marrow of BAH-1 treated mice, while a significant increase in the numbers of CFU-MK colonies was observed in the TPO plus BAH-1 treated mice. No effects of BAH-1 alone were observed on the CFU-GM, BFU-E or CFU-E colonies. The magnitude of the increase was not great for megakaryocytic progenitors in the BAH-1 treated mice compared to the TPO treated mice. These results indicate that BAH-1 alone or in combination with TPO can expand megakaryocytic progenitor cells in vivo.

TABLE 1

Bone marrow hematopoietic progenitor cell levels following the administration of BAH-1, TPO, control monoclonal antibody or TPO plus BAH-1 to myelosuppressed mice

|  | CFU-MK ($\times 10^{-3}$) | | BFU-E ($\times 10^{-3}$) | CFU-GM ($\times 10^{-3}$) |
| --- | --- | --- | --- | --- |
|  | Exp 1 | Exp 2 | Exp 1 | Exp 1 |
| Control | 0 | 0 | 2.0 ± 1.0 | 9.0 ± 1.0 |
| TPO | 10.5 ± 0.5* | 3.0 ± 1.0* | 7.0 ± 1.0 | 50.5 ± 9.5* |
| BAH-1 | 1.0 ± 0.0 | 2.0 ± 1.0* | 2.5 ± 1.0 | 12.0 ± 1.0 |
| BAH-1 + TPO | 12.0 ± 1.0* | 4.5 ± 0.5* | 7.5 ± 0.5* | N.D. |

The resulting cell levels in each experiment represent the mean ± SEM of two to three animals in each group.
*p < 0.005

Materials and Methods

Mice Treatments and Assays.

For the myelosuppression experiments, six- to nine-week old female BALB/c mice received a single intraperitoneal injection of 1.2 mg carboplatin and 350 cGy whole-body $^{137}$Cs irradiation (GAMMACELL 40 Irradiator; Atomic Energy of Canada Radiochemical Co., Kanata, Canada) on day 0. The following day, the mice were begun on daily intraperitoneal injections of vehicle (20 mM Tris, pH 8.1/ 0.9% NaCl/0.25% rabbit serum albumin), recombinant murine TPO (40 kU/mouse/d) in vehicle, purified BAH-1 antibody (5 μg/mouse), or both TPO (40ku) and BAH-1 antibody (5 μg/mouse).

Animals were sacrificed 13 to 14 days following the initiation of treatment, which was 2–3 days before the onset of platelet recovery in the TPO treated mice.

Following sacrifice by cervical dislocation, the femurs of each study mouse were harvested and single-cell suspensions were prepared using standard techniques (27–28). From 0.5 to $2 \times 10^5$ cells/ml were plated for megakaryocytic colony formation (CFU-MK) using 20 ng/ml murine IL-3 plus 7 ng/ml murine TPO in agar as previously described (8). As these cultures contained optimal levels of IL-3, granulocyte-macrophage colonies (CFU-GM) were also enumerated. Assays for erythroid bursts (BFU-E) were performed using recombinant human EPO as previously described (8). Late erythroid progenitors (CFU-E) were assayed in a plasma clot in the presence of 0.5 U/ml EPO (28). Each assay was performed in duplicate.

Growth factors. Recombinant human interleukin-3 (IL-3) or recombinant murine IL-3, human granulocyte-macrophage colony-stimulating factor (GM-CSF) and human interleukin-6 (IL-6) were obtained from R&D Systems (Minneapolis, Minn.). These cytokines were determined to be free of endotoxin contamination. Plateau doses of each factor were determined from dose-response curves. Recombinant human thrombopoietin (hTPO) or murine thrombopoietin (mTPO) (generous gifts from Genentech, Inc., South San Francisco, Calif.) were used at 100 ng/ml.

Marrow megakaryocytes. Human bone marrow was obtained by aspiration from the iliac crest of normal donors who gave informed consent in a protocol approved by the Deaconess Hospital Institutional Review Board. The marrow was aspirated into preservative-free heparin (Sigma Chemical Co., St. Louis, Mo.) and separated by centrifugation through FICOLL-HYPAQUE contintugabon and (Pharmacia Biotech, Inc., Piscataway, N.J.) at 1,200×g at room temperature for 30 minutes. After two washes with sterile phosphate-buffered saline (PBS), the cells were resuspended in Iscove's modified Dulbecco's medium (IMDM) with 20% fetal calf serum (FCS), penicillin/streptomycin (P/S) and L-glutamine; seeded onto T-75 tissue culture flasks (Corning Corp., Corning, N.Y.); and incubated at 37° C. in 5% $CO_2$. After 24 hours, the nonadherent cells were gently removed. Human marrow megakaryocytes were isolated by a method employing immunomagnetic beads using anti-human GpIIb/IIIa monoclonal antibody as described previously (11). The cells that rosetted with immunomagnetic beads were collected with a dynal magnetic particle concentrator (DYNABEADS M-450; Dynal Inc., Great Neck, N.Y.) and were washed three times with megakaryocyte (MK) medium, which consisted of $Ca^{2+}$-$Mg^{2+}$ free PBS containing 13.6 mmol/L-sodium citrate, 1 mmol/L theophylline, 1% bovine serum albumin (BSA), fraction V (Sigma Chemical Co., St. Louis, Mo.), and 11 mmol/L glucose, adjusted to pH 7.3 and an osmolarity of 290 mOSM/L. After purification, cells were labeled by a monoclonal antibody against von Willebrand factor (McAb 4F9; AMAC Inc., Westbrook, Me.) and more than 95% of the cells were stained. Twenty milliliters of bone marrow aspirate generally yielded about $1 \times 10^5$ of megakaryocytes. Contaminating cells (1–5%) were essentially monocytes and macrophages. Cells were cultured in RPMI 1640 supplemented with 2% platelet poor plasma (PPP) (11) at 37° C. in a 5% $CO_2$ fully humidified atmosphere for 24 hrs. Monocytes and macrophages were identified by morphology after May-Grunwald-Giemsa staining and by positive antibody staining using monoclonal antibody directed against CD14 (monocytes), CD15 (granulocytes), CD16 (IgG Fc receptor—natural killer [NK] cells, granulocytes and macrophages). These analyses indicated that the maximum potential degree of contamination of bone marrow megakaryocytes after 24 hr was about 5–10%.

Isolation of CD34$^+$ cells by the immunomagnetic bead technique. CD34$^+$ cells were isolated as described (12). Cells were first incubated at 4° C. for 30 minutes with the CD34$^+$ monoclonal antibody at a concentration of 10 μg/ml and then with paramagnetic beads coupled with goat antibody to mouse IgG (Dynabeads M-450; Dynal Inc., Great Neck, N.Y.) with a bead-to-target cell ratio of 5:1. CD34$^+$ cells were isolated by magnetic separation and detached from the beads by chymopapain treatment (Sigma; 130 U/mL for 10 minutes), which allows for the collection of CD34$^+$ cells which are free of beads.

Human megakaryocytic cell lines. The CMK (24) and CMS cell lines, provided by Dr. T. Sato of the Chiba University School of Medicine, Chiba, Japan and derived from megakaryoblastic leukemias, have properties of cells of megakaryocytic lineage, including surface expression of GpIb and GpIIb/IIIa, synthesis of platelet factor 4, platelet-derived growth factor and von Willebrand's factor, and become polyploid on induction with phorbol esters (25). No myeloid or lymphoid surface markers have been found on our cultured CMK cells. The CMK cell lines were cultured in RPMI 1640 medium with 10% FCS. CMS represents more primitive megakaryoblasts.

Additional permanent human megakaryocytic cell lines studied were generous gifts to our laboratory. DAMI cells were from Dr. S. Greenberg, Brigham and Women's Hospital, Boston, Mass., and Mo7e cells were from Dr. J. Hoxie, University of Pennsylvania, Pa. Each cell line was cultured as previously described (26). All other permanent human cell lines were obtained from the American Type Tissue Collection and maintained in liquid culture according to the specifications in the catalog.

Ploidy analysis of megakaryocytic cell lines. Cells were plated in 24-well plates at $2 \times 10^5$/ml, with 5% PPP for 5 days, with or without PMA, IL-6, TPO or BAH-1 antibody in various dilutions. Cells were then washed twice with Hank's Balanced Salt Solution (HBSS) and resuspended in "Nucleus Isolation Medium" (NIM—0.2% BSA, 0.4% Nonidet P40, and 10 mM HEPES pH 7.4 in HBSS) and 54 Worthington units/ml RNase A at $2 \times 10^6$/ml. An equal volume of NIM containing 25 μg/ml propidium iodide (Sigma) was then added. Samples were kept in the dark at 4° C. and analyzed the same day on a Becton-Dickinson fluorescent activated cell sorting (FACS) scan, using CELLFIT software.

Flow cytometric analysis of surface protein expression. For immunocytochemical staining (FACS staining), megakaryoblastic cell lines were used. Cells were washed with sterile PBS and $1 \times 10^6$ cells were resuspended in 0.1 ml of PBS. Cells were incubated with 10 μl of the BAH-1 monoclonal antibody, or GpIIIa antibodies (Dako Corporation, Calif.), mouse IgG as a control (Immunotech Inc., Westbrook, Me.) or PBS at 4° C. for 20 min. FITC conjugated goat anti-mouse IgG or goat anti-rabbit IgG (Boehringer Mannheim, Ind.) was added at a final dilution of 1:500 and incubated for 20 min at 4° C. Cells were washed twice and resuspended in 0.5 ml of 1% (v/v) paraformaldehyde in PBS. Cells were then analyzed by flow cytometry.

Immunoprecipitation. CMK cells ($2\times10^6$/ml) were serum starved 4–5 hrs in RPMI 1640 medium. Cells were centrifuged and then resuspended at $10^7$ cells/ml in RPMI 1640. Cells ($20\times10^6$/precipitation) were placed on ice and lysed by the addition of 1/3 vol. of 3×lysis buffer (40 mM Tris-HC1, pH 7.4; 2 mM $MgCl_2$; 2 mM $CaCl_2$; 20% glycerol; 2% NP-40; 2 mM $Na_3Vo_4$; 20 µg/ml leupeptin; 20 µg/ml aprotinin; 4 mm PMSF). Lysates were centrifuged 10,000×g for 15 min. The monoclonal antibodies BAH-1 or Mpl-R monoclonal antibody (Genzyme Corp., Cambridge, Mass.) were added to the supernatant at 5 µg/precipitation. Tubes were incubated by rocking at 5° C. for 3 hrs and then 40 µl of 1:1 Protein G-Sepharose (Pierce, Rockford, Ill.) was added. After 1½ hr, lysates were washed 3 times with 1×lysis buffer. SDS sample buffer was added to the washed beads and samples were run on SDS-PAGE (7.5% acrylamide).

Western immunoblotting. Mpl-IgG at various concentrations (0.5 to 6 µg/ml) were used for Western blot analysis. SDS polyacrylamide gels were electrophoretically transferred to nitrocellulose membranes (BioRad, Hercules, Calif.). The membranes were blocked with 4% BSA in PBS/0.1% Tween 20 (PBST) and then incubated with monoclonal antibodies (0.2 µg/ml) for 1½ hrs or with Mpl-R monoclonal antibodies (0.2 µg/ml). Membranes were then washed 3 times in PBST and incubated for 45 min in horseradish peroxidase-linked secondary antibody (Amersham Corp., Arlington Heights, Ill.) diluted in PBST. Transfers were washed 3 times in PBST and developed by the ECL Method (Amersham).

Megakaryocyte progenitor assay. Bone marrow low-density cells were cultured in a semi-solid medium using the plasma clot technique (11). The medium consisted of RPMI 1640, 1% deionized BSA, 20 µg/ml asparagine, 28 µg/ml $CaCl_2$, 10% PPP and $2.5\times10^5$ non-adherent bone marrow cells in the absence or presence of various dilution of the monoclonal antibody BAH-1. Citrated bovine plasma (Gibco, Gaithersburg, Md.) (10%) was added as the last product. PPP and citrated bovine plasma used in these cultures were assayed and determined to be devoid of any detectable IL-6 or endogenous TGF-β. Cultures were incubated for 12 days at 37° C. in duplicate. Quantitation of colonies was performed by indirect immunofluorescent ABC kit labeling using anti-GpIIIa antibodies. Each dish was entirely scanned under a fluorescent microscope at day 12 of culture, and each cluster of three or more megakaryocytes was scored as a colony. For limiting dilution experiments, $CD34^+$ cells were directly sorted into 96-well tissue culture plates, and the number of megakaryocytes were identified by a GpIIb/IIIa cell-based ELISA (11).

Murine megakaryocyte assay. To assess megakaryocytic differentiating activity, a single megakaryocyte growth assay was employed (25). Single cell populations from bone marrow were prepared from the femurs of normal C57/BL6 mice. This preparation was performed by flushing the bones with Dulbecco's modified Eagle's medium (DMEM) containing 10% FCS.

Immature megakaryocyte populations were obtained in 1.07–1.085 $gM/cm^{-3}$ fractions, from a suspension of single bone marrow cells separated in a Percoll gradient. The fractionated cells were cultured in 10% FCS in DMEM for 5 days at 37° C., in a 10% $CO_2$ humidified incubator. This procedure was performed in the presence of titrated doses of growth factors. Cultures were dried and stained for acetylcholinesterase. Immature megakaryocyte growth and maturation were quantitated by the number of single large megakaryocytes detected by light microscopy.

Statistical Analysis. The results were expressed as the mean±SEM of data obtained from three or more experiments performed in triplicate. Statistical significance was determined using the Student's t-test.

Use

As the agonist monoclonal antibodies of the invention are capable of acting as stimulants for megakaryocytopoiesis, individual monoclonal antibodies, e.g., BAH-1 and M4, will be very useful in therapeutic compositions and methods for treating patients with thrombocytopenia. The monoclonal antibody of the invention can be administered independently or in conjunction with other agents, especially in conjunction with TPO. As we have reported herein, BAH-1 and TPO do act synergistically in the expansion and generation of megakaryocytic progenitor cells. In combination therapy, the proportion of BAH-1 and TPO administered would preferably be approximately equal.

The antibody compositions of the invention can be administered using conventional modes of administration including, but not limited to, intravenous, intra-arterial, intraperitoneal, oral, intralymphatic or intramuscular. Intravenous administration is preferred. The compositions of the invention can be in a variety of dosage forms, with the preferred form depending upon the mode of administration and the therapeutic application. Optimal dosage and modes of administration for an individual patient can readily be determined by conventional protocols. An effective serum dosage of the antibody compositions of this invention may be in the range of from about 1 to about 100 µg/ml, and preferably 10 µg/ml, resulting in about 1 mg/kg patient body weight.

References

1. Lok et al., "Cloning and expression of murine thrombopoietin CDNA and stimulation of platelet production in vivo," Nature 369: 565–568 (1994).
2. de Sauvage et al., "Stimulation of megakaryocytopoiesis and thrombopoiesis by the c-Mpl ligand," Nature 369: 533–538 (1994).
3. Bartley et al., "Identification and cloning of a megakaryocyte growth and development factor that is a ligand for the cytokine receptor Mpl," Cell 77: 1117–1124 (1994).
4. Kuter et al., "The purification of megapoietin: a physiological regulator of megakaryocyte growth and platelet production," Proceedings of the National Academy of Sciences of the United States of America 91: 11104–11108 (1994).
5. Kaushansky et al., "promotion of megakaryocyte progenitor expansion and differentiation by the c-Mpl ligand thrombopoietin," Nature 369: 568–571 (1994).
6. Choi et al., "Platelets generated in vitro from proplatelet-displaying human megakaryocytes are functional," Blood 85: 402–413 (1995).
7. Broudy et al., "Thrombopoietin (c-mpl ligand) acts synergistically with erythropoietin, stem cell factor, and interleukin-11 to enhance murine megakaryocyte colony growth and increases megakaryocyte ploidy in vitro," Blood 85: 1719–1726 (1995).
8. Zeigler et al., "In vitro megakaryocytopoietic and thrombopoietic activity of c-mpl ligand (TPO) on purified murine hematopoietic stem cells," Blood 84: 4045–4052 (1994).
9. Papayannopoulou et al., "The influence of Mpl-ligand on the development of megakaryocytes from $CD34^+$ cells isolated from bone marrow peripheral blood," Blood 84: 32 (1994).
10. Wendling et al., "cMpl ligand is a humoral regulator of megakaryocytopoiesis," Nature 369: 571–574 (1994).

11. Banu et al., "Modulation of megakaryocytopoiesis by thrombopoietin: the c-Mpl ligand," Blood 86: 1331–1338 (1995).
12. Debili et al., "the Mpl-ligand or thrombopoietin or megakaryocyte growth and differentiative factor has both direct proliferative and differentiative activities on human megakaryocyte progenitors," Blood 86: 2516–2525 (1995).
13. Kaushansky et al., "Thrombopoietin, the Mpl ligand, is essential for full megakaryocyte development," Proceedings of the National Academy of Sciences of the United States of America 92: 3234–3238 (1995).
14. Gurney et al., "Thrombocytopenia in c-mpl-deficient mice," Science 265: 1445–1447 (1994).
15. Kaushansky et al., "Thrombopoietin expands erythroid progenitors, increases red cell production, and enhances erythroid recovery after myelosuppressive therapy," Journal of Clinical Investigation 96: 1683–1687 (1995).
16. de Sauvage et al., "Physiological regulation of early and late stages of megakaryocytopoiesis by Thrombopoietin," Journal of Experimental Medicine 183: 651–656 (1996).
17. Meyer et al., "Isolation and characterization of monoclonal antibodies directed against plant plasma membrane and cell wall epitopes: identification of a monoclonal antibody that recognizes extension and analysis of the process of epitope biosynthesis in plant tissues and cell cultures," Journal of Cell Biology 107: 163–175 (1988).
18. Scudder et al., "Preparation and Functional Characterization of Monoclonal Antibodies against Clycoprotein Ib," Blood 61: 99 (1983).
19. Gilbert et al., "Production of a human monoclonal anti-epithelial cell surface antibody derived from a patient with pemphigus vulgaris," Journal of Autoimmunity 5: 173–182 (1992).
20. Barclay et al., "Rapid isolation of monoclonal antibodies specific for cell surface differentiation antigens," Proceedings of the National Academy of Sciences of the United States of America 83: 4336–4340 (1986).
21. Coller, "Diagnostic and therapeutic applications of anti-platelet monoclonal antibodies," Biorheology 24: 649–658 (1987).
22. Azrin et al., "Preparation, characterization, and evaluation of a monoclonal antibody against the rabbit platelet glycoprotein IIb/IIIa in an experimental angioplasty model," Circulation Research 75: 268–277 (1994).
23. Coller et al., "A murine monoclonal antibody that completely blocks the binding of fibrinogen to platelets produces a thrombasthenic-like state in normal platelets and binds to glycoproteins IIb and/or IIIa," Journal of Clinical Investigation 72: 325–338 (1983).
24. Komatsu et al., "Growth and differentiation of a human megakaryoblastic cell line, CMK," Blood 74: 42 (1989).
25. Avraham et al., "Modulation of megakaryocytopoiesis by human basic fibroblast growth factor," Blood 83: 2126–2132 (1994).
26. Avraham et al., "Interaction of human bone marrow fibroblasts with megakaryocytes: role of the c-kit ligand," Blood 80: 1679–1684 (1992).
27. Grossmann et al., "Thrombopoietin accelerates platelet, red blood cell, and neutrophil recovery in myelosuppressed mice," Experimental Hematology 24: 1238–1246 (1996).
28. Kaushansky et al., "Thrombopoietin expands erythroid, granulocyte-macrophage, and megakaryocytic progenitor cells in normal and myelosuppressed mice," Experimental Hematology 24: 265–269 (1996).

Deposits

Hybridoma mcAbαMplambdaR, producing a monoclonal antibody having the common name BAH-1, was deposited on Jan. 24, 1996, with the American Type Culture Collection (ATCC), 10801 University Bolevard, Manassas, Va. 20110-2209, USA, as ATCC No. HB 12027.

Hybridoma BF#3, 12h8=M4, producing a monoclonal antibody having the common name M4, was deposited on May 15, 1997, with the American Type Culture Collection (ATCC), 10801 University Boulevard, Manassas, Va. 20110-2209, U.S.A., as ATCC No. HB 12353.

Applicants' assignee, Beth Israel Deaconess Medical Center, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. An agonist monoclonal antibody BAH-1 produced by the hybridoma cell line ATCC No. HB 12027; or an agonist monoclonal antibody that binds to the same antigenic determinant as a monoclonal antibody produced by the hybridoma cell line ATCC No. HB 12027; or an Fab, F(ab')$_2$, or Fv fragment or conjugate of a monoclonal antibody produced by the hybridoma cell line ATCC No. HB 12027, wherein said agonist monoclonal antibody specifically recognizes human megakaryocytes and is capable of stimulating megakaryocytopoiesis in vitro.

2. An agonist monoclonal antibody M4 produced by the hybridoma cell line ATCC No. HB 12353; or an agonist monoclonal antibody that binds to the same antigenic determinant as a monoclonal antibody produced by the hybridoma cell line ATCC No. HB 12353; or an Fab, F(ab')$_2$, or Fv fragment or conjugate of a monoclonal antibody produced by the hybridoma cell line ATCC No. HB 12353, wherein said agonist monoclonal antibody specifically recognizes human megakaryocytes and is capable of stimulating megakaryocytopoiesis in vitro.

3. The monoclonal antibody of either claim 1 or claim 2 wherein said monoclonal antibody is a human monoclonal antibody.

4. The monoclonal antibody of either claim 1 or claim 2 wherein said monoclonal antibody is a chimeric mouse-human antibody.

5. The hybridoma cell line ATCC No. HB 12027.

6. The hybridoma cell line ATCC No. HB 12353.

7. A continuous hybridoma cell line that produces an agonist monoclonal antibody, wherein said agonist monoclonal antibody binds to the same antigenic determinant as the BAH-1 monoclonal antibody produced by the hybridoma cell line ATCC No. HB 12027, specifically recognizes human megakaryocytes and is capable of stimulating megakaryocytopoiesis in vitro.

8. A continuous hybridoma cell line that produces an agonist monoclonal antibody, wherein said monoclonal antibody binds to the same antigenic determinant as the M4 monoclonal antibody produced by the hybridoma cell line ATCC No. HB 12353, specifically recognizes human megakaryocytes and is capable of stimulating megakaryocytopoiesis in vitro.

9. A therapeutic composition comprising a therapeutically effective amount of the agonist monoclonal antibody of either claim 1 or claim 2 in a pharmaceutically acceptable carrier.

10. The therapeutic composition of claim 9 further comprising a therapeutically effective amount of thrombopoietin.

11. A monoclonal antibody produced by the hybridoma cell line ATCC No. HB 12027, said monoclonal antibody being denominated BAH-1.

12. A monoclonal antibody produced by the hybridoma cell line ATCC No. HB 12353, said monoclonal antibody being denominated M4.

* * * * *

UNITED STATES PATENT AND TRADEMARK OFFICE
CERTIFICATE OF CORRECTION

PATENT NO      : 5,980,893
DATED          : November 9, 1999
INVENTOR(S)    : Hava Avraham, Jerome E. Groopman It is certified that error appears in the above-identified patent and that said Letters Patent are hereby corrected as shown below:

Column 8, Table 1, 1st column, "Control
                                TPO
                                BAH-1
                                BAH-1+
                                TPO       "

should read -- Control
                                    TPO
                                    BAH-1
                                    BAH-1 + TPO --

Column 9, line 41, "contintugabon and" should read --centrifugation aid--

Column 11, lines 57, 58 "10% FCS.    should read --10% FCS. Immature--
                        Immature"

Column 14, line 5, "Bolevard" should read --Boulevard--

Signed and Sealed this

First Day of May, 2001

Attest:

NICHOLAS P. GODICI

Attesting Officer    Acting Director of the United States Patent and Trademark Office